(12) United States Patent
Hammond et al.

(10) Patent No.: US 8,606,486 B2
(45) Date of Patent: Dec. 10, 2013

(54) SYSTEM AND METHOD FOR MEASURING ENGINE AIRFLOW

(75) Inventors: Bryant G. Hammond, West Bloomfield, MI (US); Layne K. Wiggins, Plymouth, MI (US); Jan Andrzej Gatowski, Beverly Hills, MI (US)

(73) Assignee: GM Global Technology Operations LLC

( * ) Notice: Subject to any disclaimer, the term of this patent is extended or adjusted under 35 U.S.C. 154(b) by 445 days.

(21) Appl. No.: 12/900,039

(22) Filed: Oct. 7, 2010

(65) Prior Publication Data

US 2011/0315114 A1 Dec. 29, 2011

Related U.S. Application Data

(60) Provisional application No. 61/359,103, filed on Jun. 28, 2010.

(51) Int. Cl.
*G06F 17/00* (2006.01)

(52) U.S. Cl.
USPC .......................................................... 701/103

(58) Field of Classification Search
USPC ........ 73/114.32–114.34; 123/406.45, 406.49, 123/406.55, 677, 678; 701/103
See application file for complete search history.

(56) References Cited

U.S. PATENT DOCUMENTS

| | | | | |
|---|---|---|---|---|
| 3,831,563 A | * | 8/1974 | Brittain et al. | 123/487 |
| 6,701,890 B1 | * | 3/2004 | Suhre et al. | 123/350 |
| 7,275,426 B2 | * | 10/2007 | Lahti et al. | 73/114.32 |
| 7,430,903 B2 | * | 10/2008 | Ramos | 73/204.11 |
| 8,135,503 B2 | * | 3/2012 | Parras | 701/16 |
| 2004/0113751 A1 | * | 6/2004 | Timelthaler | 338/309 |
| 2006/0134480 A1 | * | 6/2006 | Beasley et al. | 429/22 |

FOREIGN PATENT DOCUMENTS

| DE | 2305314 | 8/1973 |
|---|---|---|
| DE | 2605278 | 8/1976 |

OTHER PUBLICATIONS

Hot-Wire Anemometer:Theory, Nov. 10, 2006, eFunda Inc.*
Office Action dated Oct. 12, 2012 from the German Patent Office for German Patent Application No. 102011105411.5.

* cited by examiner

*Primary Examiner* — Stephen K Cronin
*Assistant Examiner* — Elizabeth Hadley

(57) ABSTRACT

A control system for an engine includes a density determination module and a mass air flow (MAF) determination module. The density determination module determines a density of air in an induction system of the engine based on a temperature of the air, a pressure of the air, and a relative humidity of the air. The MAF determination module, based on the determined density of the air, a velocity of the air, and a cross-sectional area of the induction system, determines a MAF through the induction system.

19 Claims, 3 Drawing Sheets

SYSTEM AND METHOD FOR MEASURING ENGINE AIRFLOW

CROSS-REFERENCE TO RELATED APPLICATIONS

This application claims the benefit of U.S. Provisional Application No. 61/359,103, filed on Jun. 28, 2010. The disclosure of the above application is incorporated herein by reference in its entirety.

FIELD

The present disclosure relates to internal combustion engines and more particularly to a system and method for measuring engine airflow.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Internal combustion engines draw air into an intake manifold through an induction system that may be regulated by a throttle. Specifically, a rate of airflow through the induction system may increase as throttle opening increases. A mass air flow (MAF) sensor measures the rate of airflow through the induction system. Measurements of the MAF sensor may indicate a load on the engine. For example, the load on the engine may vary based on driver input. The air in the intake manifold is combined with fuel to create an air/fuel (A/F) mixture. The A/F mixture is combusted within a plurality of cylinders to drive pistons that rotatably turn a crankshaft and generate drive torque.

SUMMARY

A control system for an engine includes a density determination module and a mass air flow (MAF) determination module. The density determination module determines a density of air in an induction system of the engine based on a temperature of the air, a pressure of the air, and a relative humidity of the air. The MAF determination module, based on the determined density of the air, a velocity of the air, and a cross-sectional area of the induction system, determines a MAF through the induction system.

A method includes determining a density of air in an induction system of an engine based on a temperature of the air, a pressure of the air, and a relative humidity of the air, and based on the determined density of the air, a velocity of the air, and a cross-sectional area of the induction system, determining a mass air flow (MAF) through the induction system.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
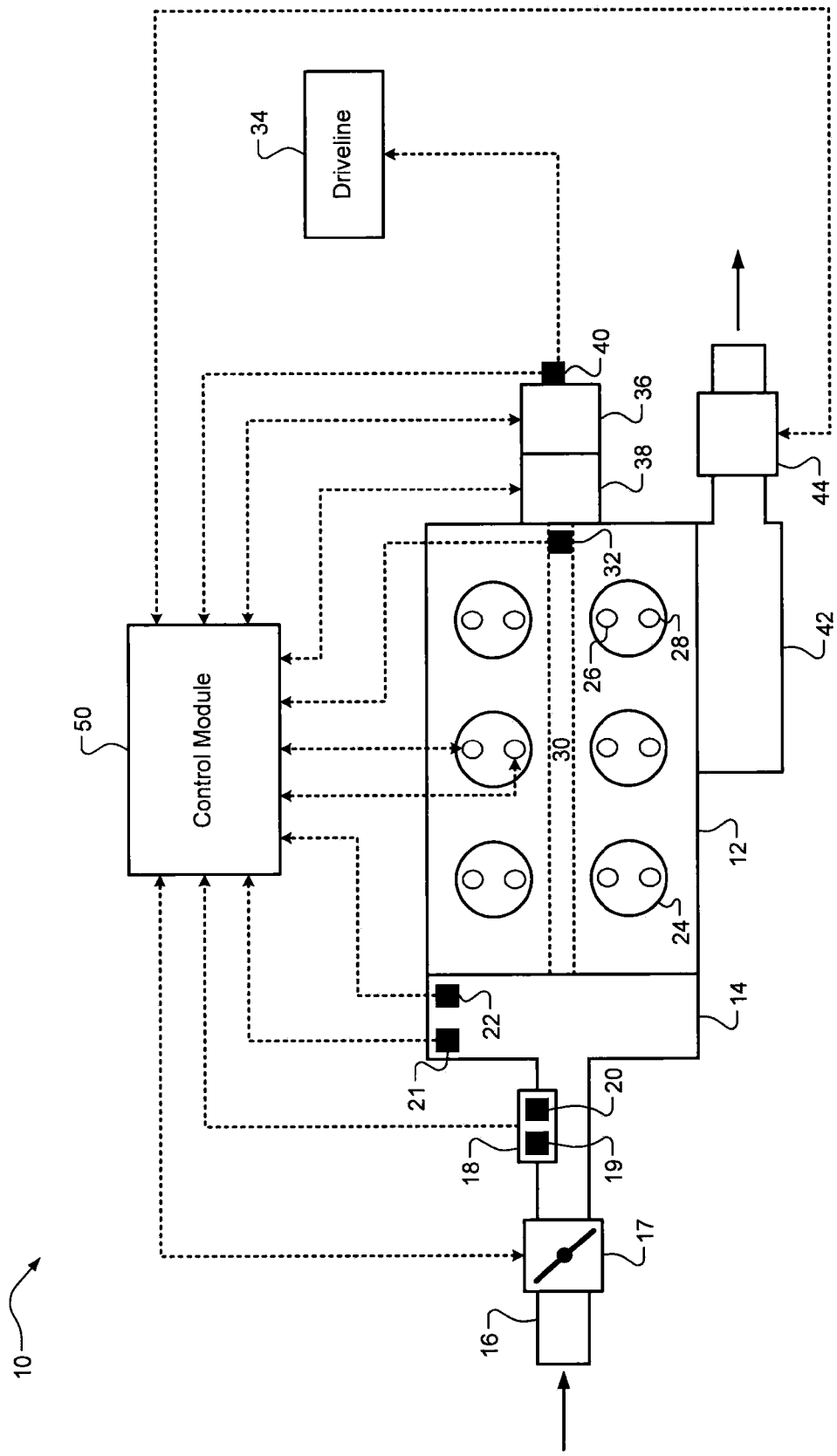
FIG. 1 is a functional block diagram of an engine system according to one implementation of the present disclosure.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Mass air flow (MAF) is based on a product of air density, air velocity, and a cross-sectional area of the induction system. In other words, MAF may be determined as follows:

$$\text{MAF} = \rho_{AIR} \times v^{AIR} \times \text{area}_{IS} \qquad (1),$$

where $\rho_{AIR}$ represents the air density, $v_{AIR}$ represents the air velocity, and $\text{area}_{IS}$ represents the cross-sectional area of the induction system. MAF, therefore, may vary between different induction systems. For example, different induction system implementations or configurations may affect at least one of the air density $\rho_{AIR}$ and the cross-sectional area of the induction system $\text{area}_{IS}$.

Accordingly, engine control systems may require calibration based on the induction system in order to correctly interpret the MAF sensor output. For example, engine control systems may be calibrated by characterizing airflow through the induction system using a sonic nozzle flow stand and conditioned air (i.e., controlled temperature, pressure, and/or relative humidity). The required calibration of engine control systems based on induction system implementation may increase costs and/or complexity of the engine control systems.

Additionally, while the cross-sectional area of the induction system may be known, the air density $\rho_{AIR}$ may vary. For example, the cross-sectional area of the induction system may be predetermined and stored in memory. For example only, the memory may include non-volatile memory (NVM). The air density $\rho_{AIR}$, however, may vary based on air temperature ($T_{AIR}$), air pressure ($P_{AIR}$), and relative air humidity ($RH_{AIR}$). Fluctuations in the air temperature $T_{AIR}$, air pressure $P_{AIR}$, and/or relative air humidity $RH_{AIR}$, therefore, may affect measurements of the MAF sensor. Inaccurate MAF measurements may decrease performance and/or fuel economy.

Accordingly, a system and method are presented for improved measurement of engine airflow. The system and method may determine air density $\rho_{AIR}$ in an induction system of an engine based on measured air temperature $T_{AIR}$, measured air pressure $P_{AIR}$, and measured relative air humidity $RH_{AIR}$. For example, the system and method may determine the air density $\rho_{AIR}$ using a lookup table. The system and method may then, based on the determined air density $\rho_{AIR}$, measured air velocity $v_{AIR}$, and cross-sectional area of the induction system area'$_s$, determine a MAF through the induction system.

For example, the MAF may be determined based on a product of the determined air density $\rho_{AIR}$, the measured air velocity $v_{AIR}$, and the cross-sectional area of the induction system area$_{IS}$. Additionally, for example, the cross-sectional area of the induction system area$_{IS}$ may be predetermined and stored in memory. The system and method may then control at least one component of the engine based on the determined MAF. For example, the system and method may control fuel injectors and/or spark plugs of the engine based on the determined MAF.

Referring now to FIG. 1, an engine system 10 includes an engine 12. For example, the engine system 10 may be used to propel a vehicle. The engine 12 may include a spark ignition (SI) engine, a compression ignition (CI) engine (e.g., a diesel engine), or a homogeneous charge compression ignition (HCCI) engine. The engine system 10, however, may also include a different type of engine and/or additional components such as in a hybrid electric vehicle or an electric vehicle. For example only, the additional components may include an electric motor, a battery system, and a generator.

The engine 12 draws air into an intake manifold 14 through an induction system 16 that may be regulated by a throttle 17. For example, the throttle 17 may be electrically controlled via electronic throttle control (ETC). A MAF-HUM device 18 may measure the air velocity $v_{AIR}$ in the induction system 16 and the relative air humidity $RH_{AIR}$ in the induction system 16. Specifically, the MAF-HUM device 18 may include a MAF sensor 19 that measures the air velocity $v_{AIR}$ and a humidity sensor 20 that measures the relative air humidity $RH_{AIR}$. For example, the humidity sensor 20 may include an analog humidity sensor or a digital humidity sensor that measures the relative air humidity $RH_{AIR}$ using capacitive sensing. Alternatively, the humidity sensor 20 may include a different type of sensor. Additionally, an intake air temperature (IAT) sensor 21 and a manifold absolute pressure (MAP) sensor 22 may measure air temperature $T_{AIR}$ and air pressure $P_{AIR}$, respectively.

The MAF sensor 19, for example, may include a hot-wire anemometer. Alternatively, the MAF sensor 19 may include a different type of sensor. Specifically, a hot-wire anemometer may include an electrically heated wire exposed to the airflow through the induction system 16. The air velocity $v_{AIR}$ affects a rate at which the wire loses heat, and thus the MAF sensor 19 may determine the air velocity $v_{AIR}$ by measuring an electrical current required to maintain the wire at a constant temperature. Additionally, the air velocity $v_{AIR}$ may vary based on air temperature $T_{AIR}$, air pressure $P_{AIR}$, and/or relative air humidity $RH_{AIR}$. For example only, the hot wire anemometer may include a resistive bridge and an operational amplifier circuit to translate the convective heat transfer to an electrical signal.

Specifically, the energy balance equation for an electrically heated wire maintained at a constant temperature in an airflow is as follows:

$$0 = I^1 R - \pi L D h \times (T_W - T_A) \tag{2}$$

where I represents a current through the wire (in amps, or A), R represents a resistance of the wire (in ohms, or Ω), L and D represent a length and a diameter of the wire, respectively, h represents a convection heat transfer coefficient (in watts per square meter degrees Celsius, or W/[m$_2$° C.]), and $T_W$ and $T_A$ represent wire temperature and ambient temperature, respectively (in ° C.).

By rearranging and substituting terms, including substituting for Nusselt, Reynolds, and Prandtl numbers, the energy balance equation may yield a relationship between MAF and voltage (i.e., an electrical signal that indicates MAF). For example, the resulting energy balance equation may be as follows:

$$V^2 = R_0(1 + \alpha T_W) \times \pi L2 \left[ b \left( \frac{\rho UD}{\mu} \right)^m \left( \frac{\mu C_p}{\kappa} \right)^{0.33} \right] \times (T_W - T_A), \tag{3}$$

where V represents the electrical signal (in volts), $R_0$ represents room temperature resistance of the heated element (in Ω), and the other parameters represent various convective heat transfer coefficients relating to the Nusselt, Reynolds, and Prandtl numbers.

The air in the intake manifold 14 may be distributed to a plurality of cylinders 24. While six cylinders are shown, the engine 12 may include other numbers of cylinders. The air may be combined with fuel from a plurality of fuel injectors 26 to create an air/fuel (A/F) mixture. For example, the fuel injectors 26 may inject the fuel into intake ports of the cylinders 24, respectively ("port fuel injection"), or directly into the cylinders 24, respectively ("direct fuel injection"). Moreover, the fuel injectors 26 may inject the fuel at different times depending on the type of engine. Specifically, HCCI engines (using "spark assist") and SI engines compress the A/F mixture using pistons (not shown) and ignite the compressed A/F mixture using spark from spark plugs 28. CI engines (e.g., diesel engines), on the other hand, inject fuel into compressed air thereby causing combustion of the compressed A/F mixture.

The combustion of the A/F mixture drives the pistons (not shown) which rotatably turn a crankshaft 30 generating drive torque. An engine speed sensor 32 may measure a rotational speed of the crankshaft 30. For example, the engine speed sensor 32 may measure the rotational speed of the crankshaft 30 in revolutions per minute (RPM). The drive torque may be transferred to a driveline 34 of the vehicle by a transmission 36. The transmission 35 may be coupled to the crankshaft 30 by a torque converter 38. For example, the torque converter 38 may include a fluid coupling. A TOSS sensor 40 measures a rotational speed of an output shaft of the transmission 36. For example, the TOSS sensor 40 may measure the rotational speed of the output shaft of the transmission 36 in RPM.

Exhaust gas resulting from combustion may be expelled from the cylinders 24 into an exhaust manifold 42. An exhaust treatment system 44 may treat the exhaust gas in the exhaust manifold 42 to decrease emissions before releasing the exhaust gas into the atmosphere. For example, the exhaust treatment system 44 may include one or more of catalytic converters, nitrogen oxide (NOx) absorbers/adsorbers, selective catalytic reduction (SCR) catalysts, and particulate matter (PM) filters. The engine system 10 may also include other systems including, but not limited to a turbocharger, a supercharger, and/or an exhaust gas recirculation (EGR) system.

A control module 50 communicates with and/or controls various components of the engine system 10. Specifically, the control module 50 may receive signals from the throttle 17, the MAF-HUM device 18 (the MAF sensor 19 and the humidity sensor 20), the IAT sensor 21, the MAP sensor 22, the fuel injectors 26, the spark plugs 28, the engine speed sensor 32, the transmission 36, the torque converter 38, the TOSS sensor 40, and/or the exhaust treatment system 44. The control module 50 may also control the throttle 17, the fuel injectors 26, the spark plugs 28, the transmission 36, the torque converter 38, and/or the exhaust treatment system 44. The control module 50 may also implement the system or method of the present disclosure.

Figure 2:
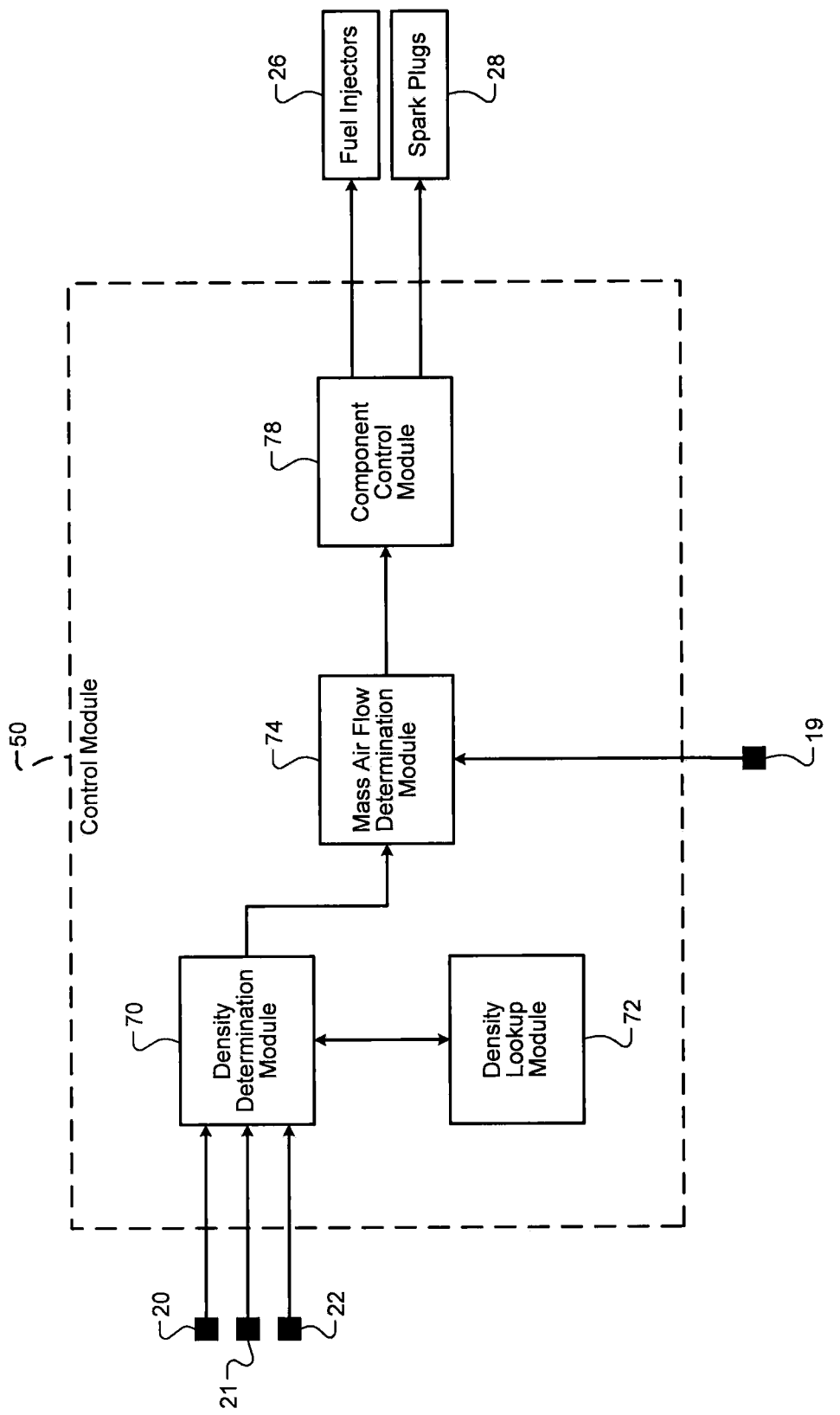
FIG. 2 is a functional block diagram of a control module according to one implementation of the present disclosure.

Referring now to FIG. 2, the control module 50 is shown in more detail. The control module 50 may include a density determination module 70, a MAF determination module 74, and a component control module 78. The control module 50 may also include memory (not shown) that stores determined and predetermined parameters. For example, the memory (not shown) may include NVM.

The density determination module 70 receives signals indicating relative air humidity $RH_{AIR}$, air temperature $T_{AIR}$, air pressure $P_{AIR}$ from the humidity sensor 20, the IAT sensor 21, and the MAP sensor 22, respectively. The density determination module 70 determines the air density $\rho_{AIR}$. Specifically, the density determination module 70 may determine the air density $\rho_{AIR}$ based on the relative air humidity $RH_{AIR}$, the air temperature $T_{AIR}$, and the air pressure $P_{AIR}$. For example, the density determination module 70 may determine the air density $\rho_{AIR}$ using a density lookup module 72 that includes a lookup table of air density $\rho_{AIR}$ based on relative air humidity $RH_{AIR}$, air temperature $T_{AIR}$, and air pressure $P_{AIR}$.

More specifically, the air density $\rho_{AIR}$ may be determined as follows:

$$\rho_{AIR} = \left(\frac{P_{AIR}}{T_{AIR} \times R_d}\right)\left(1 - \frac{0.378 \times P_V}{P_{AIR}}\right), \tag{4}$$

where $R_d$ represents a gas constant for dry air (e.g., 287.05 joules per kilograms-degrees Kelvin, or J/[kg×° K.]) and $P_v$ represents a partial pressure for water vapor (in Pascals, or Pa). For example, the water vapor partial pressure $P_v$ may be determined based on an intersection of relative air humidity $RH_{AIR}$ and air temperature $T_{AIR}$ using a psychometric chart corrected for air pressure $P_{AIR}$. Alternatively, for example, the water vapor partial pressure $P_v$ may be determined based on a product of saturation pressure (at a given air temperature $T_{AIR}$ and air pressure $P_{AIR}$) and relative air humidity $RH_{AIR}$.

The MAF determination module 74 receives the determined air density $\rho_{AIR}$ from the density determination module 70. The MAF determination module 74 may also receive a signal indicating air velocity $v_{AIR}$ from MAF sensor 19. The MAF determination module 74 determines the MAF through the induction system 16. The MAF determination module 74 may determine the MAF based on the determined air density $\rho_{AIR}$, the air velocity $v_{AIR}$, and the cross-sectional area of the induction system 16.

Specifically, the MAF determination module 74 may determine the MAF as previously described:

$$MAF = \rho_{AIR} \times v_{AIR} \times area_{IS} \tag{1}$$

The cross-sectional area of the induction system 16 $area_{IS}$ may be predetermined and stored in the memory. The cross-sectional area $area_{IS}$, however, may also be learned or input to the control module 50 using other suitable methods. More specifically, the cross-sectional area of the induction system 16 $area_{IS}$ may be defined or determined as follows:

$$area_{IS} = \frac{\pi \times D^2}{4}, \tag{5}$$

where D represents a diameter of the induction system 16 (i.e., a diameter of a duct of the induction system 16). Additionally or alternatively, therefore, the diameter D may be predetermined and stored in memory The component control module 78 receives the determined MAF from the MAF determination module 74. The component control module 78 may control various components of the engine system 10 based on the determined MAF. For example, the component control module 78 may control the fuel injectors 26 and/or spark plugs 28 based on the determined MAF. In other words, the determined MAF may indicate a load on the engine 12 and thus may represent a demand for fuel and/or spark. The component control module 78, however, may also control other components of the engine system 10 based on the determined MAF.

Figure 3:
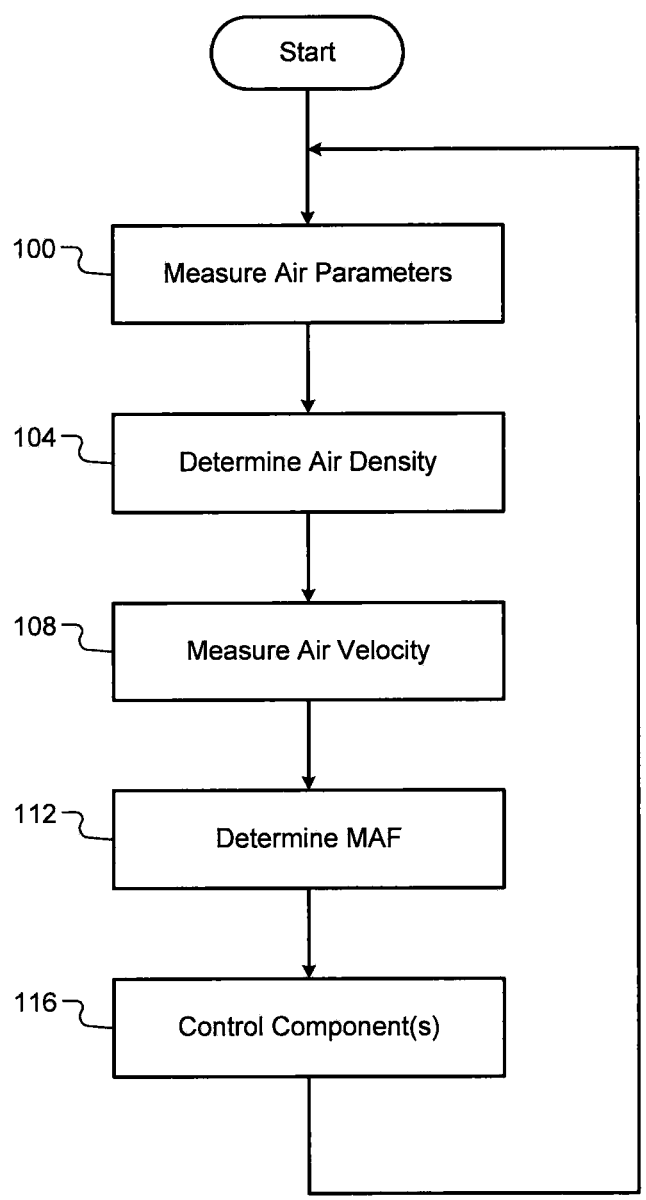
FIG. 3 is a flow diagram of a method for measuring engine airflow according to one implementation of the present disclosure.

Referring now to FIG. 3, a method for measuring engine airflow begins at 100. At 100, the control module 50 may measure air parameters. Specifically, the control module 50 may measure relative air humidity $RH_{AIR}$, air temperature $T_{AIR}$, and air pressure $P_{AIR}$. At 104, the control module 50 may determine the air density $\rho_{AIR}$ based on the measured air parameters ($RH_{AIR}$, $T_{AIR}$, $P_{AIR}$). At 108, the control module 50 may measure air velocity $v_{AIR}$.

At 112, the control module 50 may determine the MAF based on the determined air density $\rho_{AIR}$, the measured air velocity $v_{AIR}$, and the cross-sectional area of the induction system 16 ($area_{IS}$, which may be predetermined). At 116, the control module 50 may control components of the engine system 10 (e.g., fuel injectors 26, spark plugs 28, etc.) based on the determined MAF. Control may then return to 100.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A control system for an engine, comprising:
a density determination module that determines a density of air in an induction system of the engine based on a temperature of the air, a pressure of the air, and a relative humidity of the air;
a mass air flow (MAF) determination module that, based on the density of the air, a velocity of the air, and a cross-sectional area of the induction system, determines a MAF through the induction system, wherein the MAF determination module determines the MAF through the induction system based on at least one of (i) a plurality of parameters of an element in a MAF sensor, (ii) a convection heat transfer coefficient, and (iii) a difference between a temperature of the element and an air temperature; and a component control module that controls at least one component of the engine based on the determined MAF, wherein the MAF determination module determines the MAF through the induction system based on a product of (i) a sum of parameters, (ii) a product of ratios, and (iii) the difference between the temperature of the element and the air temperature.

2. The control system of claim 1, wherein the density determination module determines the density of the air using a lookup table that includes a plurality of air densities and based on the air temperature, the pressure of the air, and the relative humidity of the air.

3. The control system of claim 1, wherein the MAF determination module determines the MAF through the induction system based on a product of the air density, the velocity of the air, and the cross-sectional area of the induction system.

4. The control system of claim 1, further comprising a MAF sensor that measures the velocity of the air, wherein:
the MAF sensor includes an anemometer; and
the anemometer includes the element.

5. The control system of claim 1, further comprising a humidity sensor that measures the relative humidity of the air using capacitive-based sensing.

6. The control system of claim 1, wherein the component control module controls fuel injectors of the engine based on the MAF through the induction system.

7. The control system of claim 1, wherein the component control module controls spark plugs of the engine based on the MAF through the induction system.

8. A method, comprising:
determining a density of air in an induction system of an engine based on a temperature of the air, a pressure of the air, and a relative humidity of the air;
determining a mass air flow (MAF) through the induction system based on the density of the air,
a velocity of the air,
a cross-sectional area of the induction system,
at least one of (i) a plurality of parameters of an element in a MAF sensor, (ii) a convection heat transfer coefficient, and (iii) a difference between a temperature of the element and an air temperature, and
a product of (i) a sum of parameters, (ii) a product of ratios, and (iii) the difference between the temperature of the element and the air temperature; and
controlling at least one component of the engine based on the MAF through the induction system.

9. The method of claim 8, further comprising determining the density of the air using a lookup table that includes a plurality of air densities and based on the air temperature, the pressure of the air, and the relative humidity of the air.

10. The method of claim 8, further comprising determining the MAF through the induction system based on a product of the air density, the velocity of the air, and the cross-sectional area of the induction system.

11. The method of claim 8, further comprising measures the velocity of the air using a MAF sensor, wherein:
the MAF sensor includes an anemometer; and
the anemometer includes the element.

12. The method of claim 8, further comprising measuring the relative humidity of the air using a humidity sensor, wherein the humidity sensor measures the relative humidity of the air using capacitive-based sensing.

13. The method of claim 8, further comprising controlling fuel injectors and spark plugs of the engine based on the MAF through the induction system.

14. The control system of claim 1, wherein the MAF determination module determines the MAF through the induction system based on (i) the plurality of parameters of the element in the MAF sensor, (ii) the convection heat transfer coefficient, and (iii) the difference between the temperature of the element and the air temperature.

15. The control system of claim 14, wherein the MAF determination module determines the MAF through the induction system based on a product of:
a resistance of the element;
a length of the element;
a diameter of the element;
the convection heat transfer coefficient; and
the difference between the temperature of the element and the air temperature.

16. The control system of claim 15, wherein the MAF determination module determines the MAF through the induction system based on a thermal coefficient, a dynamic viscosity of fluid value, a thermal conductivity value, and a specific heat value.

17. The control system of claim 1, wherein the parameters in the sum of parameters include:
a resistance of the element; and
a product of (i) a constant, and (ii) the temperature of the element.

18. The control system of claim 17, wherein:
the product of ratios includes a first ratio and a second ratio;
the first ratio is between (i) a product of the density of the air, a diameter of the element, and the velocity of the air and (ii) a dynamic viscosity of fluid value; and
the second ratio is between (i) a product of the dynamic viscosity of fluid value and a specific heat value and (ii) a thermal conductivity value.

19. The method of claim 8, further comprising determining the MAF through the induction system based on a product of (i) a resistance of the element, (ii) a length of the element, (iii) a diameter of the element, (iv) the convection heat transfer coefficient, wherein
the parameters in the sum of parameters include (i) the resistance of the element, and (ii) a product of a constant and the temperature of the element,
the product of ratios includes a first ratio and a second ratio,
the first ratio is between (i) a product of the density of the air, the diameter of the element, and the velocity of the air and (ii) a dynamic viscosity of fluid value, and
the second ratio is between (i) a product of the dynamic viscosity of fluid value and a specific heat value and (ii) a thermal conductivity value.

* * * * *